United States Patent [19]

Friedli et al.

[11] Patent Number: 5,128,473
[45] Date of Patent: * Jul. 7, 1992

[54] NITROGEN-HETEROCYCLIC COMPOUNDS AND QUATERNARY SALTS THEREOF

[75] Inventors: Floyd Friedli, Dublin; Michelle Watts, Columbus, both of Ohio

[73] Assignee: Sherex Chemical Company, Inc., Dublin, Ohio

[*] Notice: The portion of the term of this patent subsequent to Jul. 7, 2009 has been disclaimed.

[21] Appl. No.: 649,493

[22] Filed: Feb. 1, 1991

[51] Int. Cl.$^5$ .............. C07D 241/04; C07D 295/00
[52] U.S. Cl. .................. 544/386; 544/374; 544/399; 544/400
[58] Field of Search ............ 544/386, 399, 400, 374

[56] References Cited

U.S. PATENT DOCUMENTS

| | | | |
|---|---|---|---|
| 3,095,373 | 6/1963 | Blomfield | 252/309 |
| 3,167,554 | 1/1965 | Ernst | 544/386 |
| 3,442,692 | 5/1969 | Gaiser | 427/242 |
| 3,634,947 | 1/1972 | Furgal | 427/242 |
| 3,676,199 | 7/1972 | Hewitt et al. | 428/341 |
| 3,686,025 | 8/1972 | Morton | 428/274 |
| 3,980,643 | 9/1976 | Kato et al. | 544/401 |
| 4,068,069 | 1/1978 | Kato et al. | 544/391 |
| 4,339,391 | 7/1982 | Hoffmann et al. | 260/401 |
| 4,459,400 | 7/1984 | Kuhfuss et al. | 528/289 |
| 4,767,547 | 8/1988 | Straathof et al. | 252/8.8 |

FOREIGN PATENT DOCUMENTS

| | | |
|---|---|---|
| 0040562 | 11/1981 | European Pat. Off. . |
| 239910 | 10/1987 | European Pat. Off. . |
| 1593921 | 7/1970 | France . |
| 1071298 | 6/1967 | United Kingdom . |

OTHER PUBLICATIONS

Lesieur Cotelle et Associes S.A. Chem Abst. 96-8527e (1982).
Hotoda et al., Chem. Abst. 105-226649s (1986).
Straathof et al., Chem. Abst. 108-58382r (1988).

*Primary Examiner*—Cecilia Tsang
*Attorney, Agent, or Firm*—Scully, Scott, Murphy & Presser

[57] ABSTRACT

New piperazine compounds of the formula

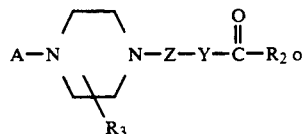

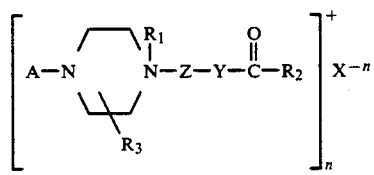

wherein
A is

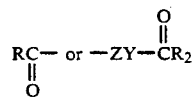

Y is —O— or —NR$_4$—;
Z is alkylene containing 2 to 6 carbon atoms in the principal chain and a total of up to 8 carbon atoms;
R is alkyl containing from about 8 to about 30 carbon atoms and may contain at least one of —S—, —O—,

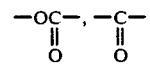

CONR$_4$, epoxy and double bond in the chain;
R$_2$ is alkyl containing up to about 30 carbon atoms and may contain at least one of —S—, —O—, .

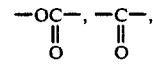

—CONR$_4$—, epoxy and double bond in the chain; and
R$^3$ and R$^4$ are each H or lower alkyl;
with the proviso that the total number of carbon atoms in the acyl R and R$_2$ groups is at least 18;
X is a salt-forming anion; R$_1$ is H, lower alkyl, hydroxylower- alkyl or benzyl; and n is an integer from 1 to 4 are especially effective as fabric softeners with antistatic properties and in hair conditioner compositions.

20 Claims, No Drawings

NITROGEN-HETEROCYCLIC COMPOUNDS AND QUATERNARY SALTS THEREOF

The present invention relates to new rapidly biodegradable compositions which exhibit hydrolytic stability upon storage. These compounds which are amides and preferably include ester groups and their salts are useful as fabric softener compositions with antistatic properties and in hair conditioner compositions.

BACKGROUND OF THE INVENTION

Fabric conditioning for improved softening and antistatic properties is normally achieved by any of general methods including, for example, the addition of a fabric softening agent to the rinse cycle of a normal wash routine; the use of a substrate impregnated with a fabric conditioner composition for use in the dryer where the fabric conditioning agent is transferred to the clothes in the dryer; and the inclusion of the fabric softening agent with a detergent formulation for the wash cycle.

Commercial fabric conditioner formulations are most commonly based on quaternary ammonium salts. Formulations for use in the final clear water rinse, and dryer and detergent softeners, are normally based on difatty dimethyl quaternary salts, for example, dihydrogenated tallow dimethyl ammonium chloride (Adogen 442, Sherex Chemical Co., Inc.) or diamidoamine quaternary (Varisoft 222 Sherex Chemical Co., Inc.) or imidazoline based quaternaries.

Within recent years, there has developed a need for fabric softening compositions with faster biodegradation. Quaternary compounds with long chain alkenyl groups interrupted by ester groups are known, from e.g., French Patent 1,593,921. Softening compositions containing such materials are disclosed in European Patent No. 0 040 562.

U.S. Pat. No. 4,767,547 claims to attain rapid biodegradation by the inclusion of ester groups in long chain substituents of quaternary ammonium compounds. Similarly, U.S. Pat. No. 4,339,391 discloses esters based on hydroxyalkyl ammonium quaternary salts. U.S. Pat. No. 3,167,554 describes the reaction of a piperazine with polybasic acids to form polyamides with specific reference to the reaction between polybasic acids and hydroxyethyl piperazine wherein the amide formation is carried out under conditions which inhibit esterification of the hydroxy group.

U.S. Pat. Nos. 4,068,069 and 3,980,643 disclosed the preparation of esters of hydroxy alkyl piperazine using conditions which cause only esterification with no amide formation.

The present invention provides compositions containing quaternary ammonium salts which rapidly biodegrade, but are sufficiently shelf stable for commercial utility. The invention further provides quaternary salts having satisfactory softening properties for rinse cycle, dryer cycle, or wash cycle use while displaying acceptable biodegration coupled with sufficient shelf stability.

SUMMARY OF THE INVENTION

The present invention relates to the amines of structure I and to their salts:

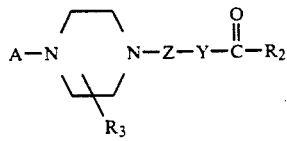

wherein A is

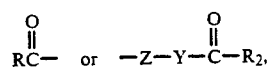

Y is O or $NR_4$; R is 8-30 alkyl or 8-30 alkyl containing at least one of —S—, —O—,

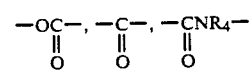

epoxy group and double bond in the chain; each $R_2$ is 1-30 alkyl or 8-30 alkyl containing at least one of —S—, —O—,

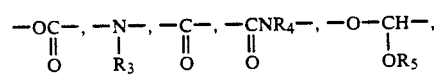

double bond, and epoxy group in the chain with the proviso that the total number of carbon atoms in the acyl R groups (i.e., R and $R_2$) is at least 18, and preferably above 30, $R_3$ and $R_4$ are each H or lower alkyl; and Z is alkylene containing 2-6 carbon atoms in the principal chain and up to a total of 8 carbons and salts thereof, including acid addition (HX) and quaternary ($R_1X$) salts, where $R_1$ is lower alkyl, hydroxy lower alkyl or benzyl and X is a salt forming anion.

Compounds of this invention are readily prepared by known procedures. The present products are prepared from

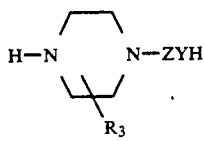

and

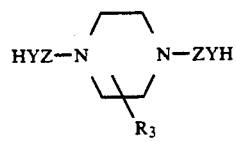

wherein Z and Y have the same meaning as previously described, by reaction of suitable acids of the formula $RCO_2H$ and $R_2CO_2H$ or acylating derivatives thereof. Thus, there can be prepared compounds of the following formulae:

TABLE II

| Structure | |
|---|---|
| Ia | R—C(=O)—N(piperazine-R3)—N—Z—O—C(=O)—R2 |
| Ib | R2—C(=O)—N—Z—N(piperazine-R3)—N—Z—N—C(=O)—R2 |
| Ic | R2—C(=O)—O—Z—N(piperazine-R3)—N—Z—N—C(=O)—R2 |
| Id | R2—C(=O)—O—Z—N(piperazine-R3)—N—Z—O—C(=O)—R2 |
| Ie | R—C(=O)—N(piperazine-R3)—N—Z—N—C(=O)—R2 |

Compounds of Structure Ia where R and $R_2$ are the same are prepared by reaction of two moles of acid, or acylating derivatives thereof, of the formula $RCO_2H$ with N-hydroxyalkylpiperazine; where R and $R_2$ differ, the compound is prepared by reaction of an acid, or acylating derivatives thereof, of formula $R_2CO_2H$ with a piperazine of the formula:

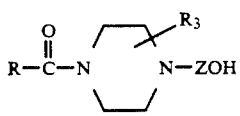

which latter compound can be prepared by acylation of the N-hydroxyalkylpiperazine with an acid or acylating derivative of the formula $RCO_2H$, under conditions which inhibit ester formation.

Compounds of Structure Ib are prepared by reaction of N,N bis(aminoalkyl) piperazine with acid or acylating derivatives thereof of the formula $R_2CO_2H$ under amide-forming conditions; where the two $R_2$ groups of the compound are the same, two equivalents of the acylating agent are used. Where the $R_2$'s differ, stepwise amidation should be used.

Compounds of Structure Ic where the $R_2$'s are the same are prepared by reacting N-hydroxylalkyl N'-aminoalkylpiperazine with two equivalents of the acylating agent employed. Where the $R_2$'s differ, the acylating proceeds stepwise with one equivalent of acylating agent forming the amide, and the second equivalent forming the ester.

Compounds of Structure Id are prepared by a similar procedure as described for Ib, but employing N,N-bis(-hydroxyalkyl)piperazine as the starting material.

Compounds of Structure Ie are prepared by a similar procedure as described for Ia, but employing the aminoethylpiperazine as the starting material.

The salts of the compounds of this invention are prepared by standard precedures, i.e., by reaction of the tertiary amine with HX or $R_1X$ in which X is a salt-forming anion and $R_1$ is loweralkyl, hydroxyloweralkyl or benzyl. X can be sulfate, ethylsulfate, carbonate, borate, phosphate, halide, carboxylate and the like. Preferred anions are chloride and methyl sulfate.

Preferred compounds include compounds of Structure Ia, Id and Ie, and salts thereof, particularly those wherein R and $R_2$ are long chain alkyls of $C_{12-22}$, Z is —$(CH_2)_2$— and $R_3$ is H, which are readily prepared by quaternization of the aforesaid tertiary amine with diethyl sulfate, dimethyl sulfate or methyl chloride or, alternatively, by reaction with a dialkylcarbonate, i.e., dimethylcarbonate, followed by reaction with a suitable acid, such as phosphoric, sulfuric, lower alkanoic acid or hydroxylower-alkanoic acid, e.g., lactic acid. Most preferred are compounds of Structure Ia.

The acids or derivatives used for acylation to amide or ester groups include alkanoic acids from $C_2$ through $C_{22}$, saturated or unsaturated, substituted or unsubstituted.

Especially suitable are fatty acids derived from naturally-occurring animal and vegetable or fish oils. The acids can readily be obtained by hydrolysis of the naturally-occurring triglycerides. The acids can be converted to their acylating derivatives by halogenation to acyl halides, or by esterification/transesterification to the lower alkyl, e.g., methyl, esters, or by anhydride formation, including anhydrides formed with lower alkanoic acids such as acetic acid. The acids or their acylating derivatives can be used with retention of the unsaturation found in the natural products or the unsaturation can be reduced or eliminated entirely by hydrogenation. Hydroxy substituted fatty acid can be obtained from castor oil, i.e., 12-hydroxyoleic acid. Unsaturated acids such as oleic (cis octadecenoic acid) can be epoxidized to epoxystearic acid by use of peroxides or peracids.

The following examples further illustrate the present invention.

PREPARATION OF THE ESTER AMIDE

Two moles of the desired fatty acid were placed in a 2-liter 4-neck flask. The flask was fitted with an addition funnel, air condenser, thermometer, and mechanical stirrer. The flask was heated until the acid was melted and then 1 mole (150 g) of 1-(2-hydroxyethyl) piperazine was added dropwise via the addition tunnel. Immediately upon addition, the solution turned dark brown. After addition was complete, the flask was heated to 150°-170° C. and the reaction was monitored by change in acid value. Periodically, the reaction was submitted to a water aspirated vacuum to remove water from the system. A typical preparation usually took between 8 and 12 hours. After completion of the reaction, the hot molten material was poured into two separate 1-liter Erlenmeyer flasks and allowed to cool to room temperature.

After cooling, the material solidified. The solid material was dissolved in methylene chloride (or toluene) and $MgSO_4$ was added to the organic solution to remove any remaining water. The solution was filtered and the organic solvent removed in vacuo. The residual solid was recrystallized from ethyl acetate. Acid values ranged from 2-6 (theoretical 0.0). Total amine values (TAV) ranged from 95-110 for the myristic acid derivative (theoretical 84.7). IR data showed two carbonyl bands at 1735 cm$^{-1}$ (ester carbonyl) and 1655 cm$^{-1}$ (amide carbonyl). No amine or hydroxyl bands were found. C-13 NMR confirmed the desired structure.

QUATERNIZATION OF ESTER AMIDE

The ester amide of 1-(2-hydroxyethyl) piperazine, 0.578 mole, 370 ml of isopropyl alcohol, and 64 g of $NaHCO_3$ was placed in a 2-liter Parr reactor. The reactor was sealed and methyl chloride was charged into the reactor while stirring until the temperature and pressure stabilized (usually at 30° C. and 50 psi). The reactor was heated to 100° C. and the reaction was monitored by TAV. Reaction times were normally between 6 and 8 hours. After the reaction was complete, the reactor was cooled to 80° C. and vented. The resulting mixture was vacuum filtered and the resulting filtrate was evaporated to dryness. Typical yields ranged from 95-100% for the myristic acid derivative and 91-93% for the stearic acid derivative. Wet analysis is shown in Table I.

TABLE I

Analytical Results of Quaternization of Hydroxyethyl Piperazine Ester Amide

|        | C14 Esteramide | C18 Esteramide |
|--------|----------------|----------------|
| % FA   | 1.8%           | 2.3%           |
| % AHH  | 1.8%           | 0.0%           |
| % Quat | 99.1%          | 83% (15% IPA)  |

FA = fatty acid
AHH = amine hydrohalide
Quat = quaternary salt

IR data showed both carbonyl peaks present (1730 and 1645 cm$^{-1}$) $C^{13}$ NMR data shows new peak at 48.56 ($CH_3$—N) and thus confirmed the structure. Chemical shifts of the other carbons were consistent with quaternary formation.

BIODEGRADATION

The compounds of this invention exhibit surprisingly rapid biodegradation. The compound of Formula I where Z is 2; Y is O; R and $R_2$ are $C_{17}$ alkyl chains derived from hardened tallow; $R_3$ is H; converted to its quaternary salt with $R_1X$ where $R_1$ is methyl; and X is Cl-(Structure II) was evaluated for biodegradation according to the following scheme:

The quaternary salts evaluated were di(hydrogenated tallow) dimethylammonium chloride (Adogen ® 442, Structure III); ditallow dimethylammonium chloride (Adogen ® 470, Structure IV); distearyl dimethyl ammonium chloride (Arosurf ® TA 100, Structure V); methyl, tallowamidoethyl, 2-tallowimidazolinium methyl sulfate (Varisoft ® 475, Structure VI); methyl, bis (tallowamidoethyl), 2-hydroxy ethyl ammonium methylsulfate (Varisoft ® 222, Structure VII); lauryltrimethyl ammonium methylsulfate (Structure VIII), all of which are listed in Table III.

All compounds were obtained from Sherex Chemical Co. (Dublin, Ohio). The compounds with trade names in parentheses were used as supplied; the others were purified by recrystallization from appropriate solvents. The bacteria were obtained as Polyseed (Polybac Corp.). Polyseed is a mixture of 12 bacteria which are characteristic of those found in wastewater and POTW. HPLC grade water was used (Fisher) and dissolved oxygen was measured with a dissolved oxygen probe and meter (Yellow Springs Instruments, Model 58). Biodegradation samples were incubated at 20+/−0.3° C. in the dark. Absorbance measurements were carried out using a UV-Visible spectrophotometer (Hewlett Packard Model 8452A).

ACCLIMATION OF BACTERIA

A capsule containing Polyseed was dispersed into 250 ml dilution water where the oxygen level in the water was 15.0+/−0.2 mg/l. If the oxygen level was below 15 mg/l, the water used was standard APHA dilution water as described in the standard methods. The nutrient solution was prepared from 25 g peptone, 15 g beef extract, 4 g urea, 4 g glucose, and 3 g $KH_2PO_4$ dissolved into 1000 ml HPLC grade water. Over a five day period, the bacteria were given less nutrient solution and more QAC solution until the bacteria were not receiving any nutrient solution. On the first day the bacteria were fed 1 ml of nutrient solution and 10 mg of QAC. On the second day 1 ml of nutrient solution and 20 mg QAC was added to the culture along with 20 mg of quaternary ammonium compound (QAC). On the fourth day of 0.5 ml of nutrient solution and 80 mg QAC was added. On the fifth day 0.2 ml nutrient solution was added, along with 100 mg QAC and 1 ml diammonium phosphate solution at a concentration of 24 g/l water. Fifty ml aliquots of HPLC water with a dissolved oxygen level of 15 mg/$O_2$/l were added to the cultures each day after the first day. After the five day period 2 ml aliquots of the bacteria are immediately used in closed bottle testing.

METHOD

The procedure used for biodegradation evaluations is a variation of the Closed Bottle of Biochemical Oxygen Demand (BOD) method. The method used is as described in Method 507 of the Standard Methods for the Examination of Waste and Wastewater; 15th ed., 1980) with the following exceptions: Classically the closed bottle test has been performed with activated sludge as the source of bacteria. We have chosen to used Polyseed to reduce the contribution of variable bacterial populations to experimental error. The bacterial composition is consistent within a lot of Polyseed and lot to lot variability was small. To eliminate any contribution to oxygen demand by organic materials in the water, HPLC grade water was used.

Acclimation of bacteria is one of the key factors in determining the biodegradability of QAC's. The bacteria used in each closed bottle test were acclimated over a five day period as noted above. When tests were repeated, new acclimated bacteria were prepared.

Each round of testing included a water control, a seed correction, a glucose/glutamic acid control, and a series of QAC's. All of the samples were incubated in the dark at 20° C. Dissolved oxygen measurements were taken periodically, typically every 5, 10, 15, 20, 25 and 28 days. Tests were considered invalid if any one of the controls failed; failure was indicated by: (1) The dissolved oxygen level in the water control changed more than 0.2 mg/l over a period of five days, or (2) the seed correction sample showed a depletion outside the range 0.6-1.0 mg/l over the same five-day period. Biochemical oxygen demand values were not calculated, rather calculations of % biodegradation were conducted using the ratios of biochemical oxygen depletion (mg $O_2$ depleted/mg sample) to calculated oxygen depletion (theoretical-based on empirical formula of primary molecule) or chemical oxygen depletion (experimental-based on elemental analysis).

Comparative data were obtained for ammonium quaternary salts using the same procedure and the results are shown in Table III based on the 20 day measurement.

These data show the surprising rapidity of the initial stages of biodegradation of the compounds of this invention when compared to other compounds having good softening properties. Although these and other compounds are presumed to ultimately degrade to completion, the compounds of this invention exhibit the unexpected and valuable characteristics of rapid early stage biodegradation.

competitive structures which have good softening performance.

The compounds of this invention show high utility in softening fabric in household or industrial washing routines. They can be dried and incorporated as powder in formulated detergents for use during the wash cycle; they can be added as a dispersion to the rinse cycle; or they can be supported on an inert fabric carrier for deposition during the drying operation, all by methods well known to the art. The physical characteristics of the compounds of this invention can be modified by selection of the fatty chains, and the substituents $R_1$ and $R_4$.

The compounds of this invention were evaluated for their softening ability according to the following procedures standardized by the Chemical Specialities Manufacturers Association (CSMA).

TABLE III

| Structure | Structure | % Degraded (20 day test) | Softening Ability |
|---|---|---|---|
| $[STC-N(CH_3)(ring)N-CH_2CH_2OC(ST)]^+ Cl^-$ | II | 43 | Above average |
| $[C_{13}C(O)-N(CH_3)(ring)N-CH_2CH_2OCC_{13}]^+ Cl^-$ | IIa | 72 | Above average |
| $[(HT)_2-N(CH_3)_2]^+ Cl^-$ | III | 20 | Excellent |
| $[(ST)_2-N(CH_3)_2]^+ Cl^-$ | IV | 38 | Excellent |
| $[T-N(CH_3)_3]^+ Cl^-$ | V | 64 | Below average |
| [di T imidazoline]$^+$ MeSO$_4^-$ | VI | 47 | Above average |
| $[(T-C(O)-NHCH_2CH_2)_2-N(CH_3)-CH_2CH_2OH]^+$ MeSO$_4^-$ | VII | 48 | Average |
| $[CH_3(CH_2)_{11}-N(CH_3)_3]^+ Cl^-$ | VIII | 86 | Below average |

HT = hardened tallow acid residue
T = unhardened tallow acid residue
ST = stearic acid residue (91% $C_{18}$)

It can be seen from Table III that the compound of this invention compares favorably in biodegradation to

| Procedure | Designated Test |
|---|---|
| Fabric Treatment | DCC-13A |
| Softener Evaluation | DCC-13B |
| Static Control | DCC-F |

FORMULATION OF SOFTENER FOR EVALUATION

A 6% dispersion of Structure II in isopropyl alcohol (IPA) (76.4% solids, 23.6% IPA) was formulated into a rinse cycle softening system as follows:

| Ingredients | Net % |
|---|---|
| Formula II | 8.1 |
| Nonionic (Neodol 25-9) | 1.0 |
| 150 ppm H$_2$O (160° F.) | 90.9 |

Procedure

1. Add water to a tared beaker
2. Heat in microwave oven to 160° F.
3. Place beaker with water under a lab mixer and agitate at 500 RPM.
4. Add nonionic and allow to stir 1-2 minutes.
5. Add quat (Formula II) and allow dispersion to cool to room temperature (R/T). Continue agitation.
6. Stop agitation, place beaker on balance and add R/T dilution water until desired total weight.
7. Place beaker back under lab mixture and agitate dispersion 5-10 minutes longer.

Results of the softening evaluation according to DCC-13A and 13B were as follows based on three days of testing using eight panelists per day (4 best, 1 worst) are shown in Table IV.

TABLE IV

| Formula | Day 1 | Day 2 | Day 3 | Average |
|---|---|---|---|---|
| III | 3.5 | 3.6 | 3.6 | 3.6 |
| II | 2.8 | 2.8 | 2.2 | 2.6 |
| VI | 2.3 | 2.4 | 2.3 | 2.3 |
| VII | 1.5 | 1.6 | 2.1 | 1.7 |

DIAMIDE (Structure Ie)

The compound of this invention where Y is NR$_4$, R and R$_2$ are C$_{17}$ alkyl chains derived from hardened tallow; R$_3$ and R$_4$ are H; Z is ethylene, R$_1$ is methyl and; X is MeSO$_4$ $$\text{hard tallow-}\overset{O}{\overset{\|}{C}}-N\underset{\diagdown\diagup}{\overset{\diagup\diagdown}{\phantom{x}}}\overset{+}{N}-(CH_2)_2-\overset{H}{\underset{|}{N}}-\overset{O}{\overset{\|}{C}}\text{ hard tallow} \quad \text{Formula X}$$
$$\underset{CH_3}{}$$
$$MeSO_4^-$$

PREPARATION OF DIAMIDE

Two moles of fatty acid are weighed into a round bottom reaction flask. One mole of aminoethylpiperazine (AEP) is weighed into an addition funnel. A mechanical stirrer, thermometer, N$_2$ sparge tube, and a water trap are provided. The fatty acid is melted at a temperature of 70°-80° C., under nitrogen blanket. When the acid is thoroughly melted, the mass is heated to 105°-100° C., and AEP is slowly added. An exotherm will raise the temperature approximately 10°-20° C.

When all the amine is added, raise the temperature to 165°-170° C. Maintain nitrogen sparge to remove water from the system. The reaction is followed by acid value determination. The reaction is considered complete when the acid value is ten or less.

PREPARATION OF METHYL SULFATE QUAT FORMULA X

One mole of the above diamide is weighed into a four neck round bottom flask. To that one mole, add enough IPA to make a 50% solids solution. The flask is equipped with a mechanical stirrer, thermometer, and condenser. To maintain a good color, 0.95 mole of dimethyl sulfate (DMS) is used; DMS is added via an addition tunnel. Heat the diamide/IPA mixture to 80° C. When the temperature is reached, slowly add the DMS (exothermic). When the DMS is all added, heat for one hour. The reaction is followed by acid and amine values. The Formula X product was evaluated for softening according to CSMA procedure DCC-13 A&B against Adogen 442 (Formula III) and an unsoftened control.

TABLE V

| Softener | Panel 1 | Panel 2 | Average |
|---|---|---|---|
| Structure III | 3.6 | 3.9 | 3.8 |
| Structure X | 3.0 | 2.5 | 2.8 |
| Control | 1.3 | 1.0 | 1.2 |

Table VI describes compound types within the scope of this invention.

TABLE VI $$\left[ \begin{array}{c} R_3 \\ O \phantom{xx} /\phantom{x} \phantom{x} O \\ \| \phantom{x} /\!\!\!\diagdown \phantom{x} + \phantom{x} \| \\ RC-N \phantom{xx} N-ZYCR_2 \\ \phantom{xx}\diagdown\!\!\!\diagup \phantom{x} | \\ \phantom{xxxxx} R_1 \end{array} \right] X^-$$

| R | R$_2$ | R$_1$ | R$_3$ | Z | Y | X | Structure |
|---|---|---|---|---|---|---|---|
| T | T | Me | — | C$_2$H$_4$ | O | Cl$^-$ | XI |
| T | T | Me | — | C$_3$H$_7$ | O | A$^-$ | XII |
| T | T | Me | — | C$_2$H$_4$ | O | lactate | XIII |
| T | T | Me | — | C$_2$H$_4$ | O | MeSO$_4^-$ | XIV |
| IS | IS | Me | — | C$_2$H$_4$ | O | A$^-$ | XV |
| T | T | Me | — | C$_2$H$_4$ | O | AcO$^-$ | XVI |
| CS | CS | Me | — | C$_2$H$_4$ | O | A$^-$ | XVII |
| EO | EO | Me | — | C$_2$H$_4$ | O | A$^-$ | XVIII |
| oleyl | oleyl | Me | — | C$_2$H$_4$ | O | A$^-$ | XIX |
| T | T | Me | Me | C$_2$H$_4$ | NR$_4$ | Cl$^-$ | XX |

T is tallow (hydrogenated or non-hydrogenated) acid chain (C$_{15}$-C$_{17}$).
IS is isostearic acid chain.
X$^-$ is any anion including Cl$^-$, Br$^-$, MeSO$_4^-$, R$_1$CO$_3^-$, (R$_3$)$_2$PO$_4^-$; R$_1$CO$_2^-$.
EO is epoxy oleyl.
CS is castor acids (12-hydroxyoleic).

What is claimed is:

1. A compound of the formula:

$$A-N\underset{\diagdown\!\!\diagup}{\overset{\diagup\!\!\diagdown}{\phantom{x}}}N-Z-Y-\overset{O}{\overset{\|}{C}}-R_2 \text{ or}$$
$$\phantom{xxxxxx}|$$
$$\phantom{xxxxx}R_3$$

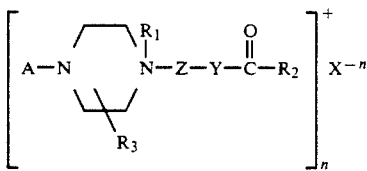

wherein
A is

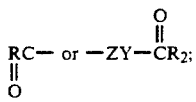

Y is —O— or —NR$_4$—;
Z is alkylene containing 2 to 6 carbon atoms in the principal chain and a total of up to 8 carbon atoms;
R is alkyl containing from about 8 to about 30 carbon atoms and may contain at least one of —S—, —O—,

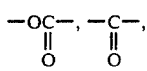

CONR$_4$, epoxy and double bond in the chain;
R$_2$ is alkyl containing up to about 30 carbon atoms and may contain at least one of —S—, —O—,

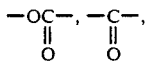

—CONR$_4$—, epoxy and double bond in the chain; and
R$_3$ and R$_4$ are each H or lower alkyl;
with the proviso that the total number of carbon atoms in the acyl R and R$_2$ groups is at least 18;
X is a salt-forming anion;
R$_1$ is H, lower alkyl, hydroxyloweralkyl or benzyl; and
n is an integer from 1 to 4.

2. A compound according to claim 1 wherein Y is —O—.

3. A compound according to claim 1 wherein X is chloride.

4. A compound according to claim 1 wherein X is alkyl carbonate.

5. A compound according to claim 1 wherein X is alkylsulfate.

6. A compound according to claim 1 wherein X is R$_3$CO$_3$—.

7. A compound according to claim 1 wherein R is alkyl containing from about 14 to about 22 carbon atoms:

8. A compound according to claim 2 wherein R$_2$ is alkyl containing from about 14 to about 22 carbon atoms.

9. A compound of the formula:

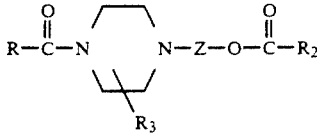

or

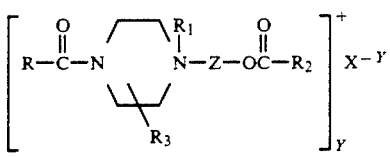

wherein
Z is alkylene containing 2 to 6 carbon atoms in the principal chain and a total of up to 8 carbon atoms;
R is alkyl containing from about 8 to about 30 carbon atoms and may contain at least one of —S—, —O—,

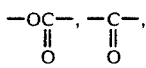

—CONR$_4$—, epoxy and double bond in the chain;
R$_2$ is alkyl containing up to about 30 carbon atoms and may contain at least one of —S—, —O—,

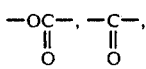

—CONR$_4$—, epoxy and double bond in the chain;
R$_3$ and R$_4$ are each H or lower alkyl;
with the proviso that the total number of carbon atoms in the acyl R and R$_2$ groups is at least 30;
X is a salt-forming anion;
R$_1$ is H, lower alkyl, hydroxyloweralkyl or benzyl; and
Y is an integer from 1 to 4.

10. A compound according to claim 9 wherein X is chloride.

11. A compound according to claim 9 wherein X is R$_3$CO$_3$—.

12. A compound according to claim 9 wherein X is methylsulfate.

13. A compound of the formula:

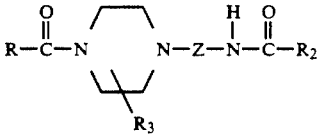

or

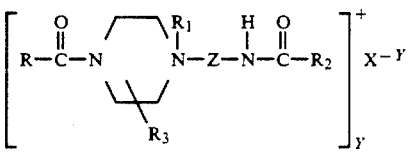

wherein

Z is alkylene containing 2 to 6 carbon atoms in the principal chain and a total of up to 8 carbon atoms;
R is alkyl containing from about 8 to about 30 carbon atoms and may contain at least one of —S—, —O—,

—OC—, —C—,
 ‖      ‖
 O      O

—CONR$_4$—, epoxy and double bond in the chain;
R$_2$ is alkyl containing up to about 30 carbon atoms and may contain at least one of —S—, —O—,

—OC—, —C—,
 ‖      ‖
 O      O

—CONR$_4$—, epoxy and double bond in the chain;
R$_3$ and R$_4$ are each H or lower alkyl;
with the proviso that the total number of carbon atoms in the acyl R and R$_2$ groups is at least 30;
X is a salt-forming anion;
R$_1$ is lower alkyl, hydroxyloweralkyl, or benzyl; and
Y is an integer from 1 to 4.

14. A compound according to claim 13 wherein X is chloride.

15. A compound according to claim 13 wherein X is R$_3$CO$_3^-$.

16. A compound according to claim 13 wherein X is methylsulfate.

17. A compound of the formula:

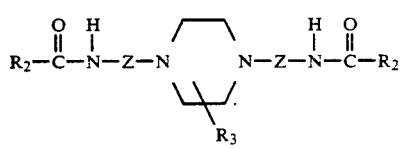

or

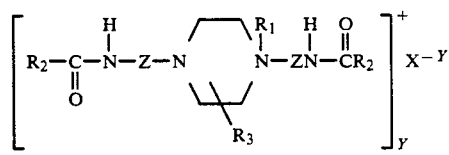

wherein
Z is alkylene containing 2 to 6 carbon atoms in the principal chain and a total of up to 8 carbon atoms;
R$_2$ is alkyl containing up to about 30 carbon atoms and may contain at least one of —S—, —O—,

—OC—, —C—,
 ‖      ‖
 O      O

—CONR$_4$—, epoxy and double bond in the chain;
R$_3$ and R$_4$ are each H or lower alkyl;
with the proviso that the total number of carbons in the two acyl R$_2$ groups is at least 30;
X is a salt forming anion;
R$_1$ is H, lower alkyl, hydroxyloweralkyl or benzyl; and
Y is an integer from 1 to 4.

18. A compound of the formula:

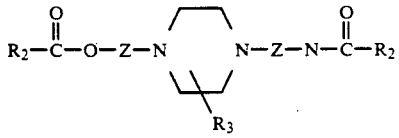

or

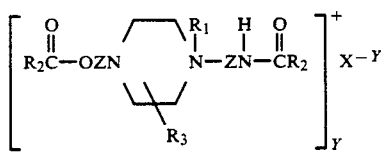

wherein
Z is alkylene containing 2 to 6 carbon atoms in the principal chain and a total of up to 8 carbon atoms;
R$_2$ is alkyl containing up to about 30 carbon atoms and may contain at least one of —S—, —O—,

—OC—, —C—,
 ‖      ‖
 O      O

—CONR$_4$—, epoxy and double bond in the chain;
R$_3$ and R$_4$ are each H or lower alkyl;
with the proviso that the total number of carbons in the two acyl R$_2$ groups is at least 30;
X is a salt-forming anion;
R$_1$ is lower alkyl, hydroxyloweralkyl or benzyl; and
Y is an integer from 1 to 4.

19. A compound of the formula:

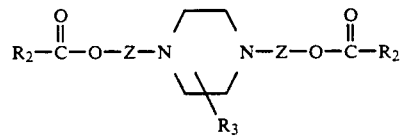

or

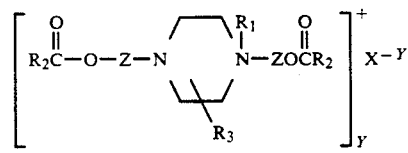

wherein
Z is alkylene containing 2 to 6 carbon atoms in the principal chain and a total of up to 8 carbon atoms;
R$_2$ is alkyl containing up to about 30 carbon atoms and may contain at least one of —S—, —O—,

—OC—, —C—,
 ‖      ‖
 O      O

—CONR$_4$—, epoxy and double bond in the chain;
R$_3$ and R$_4$ are each H or lower alkyl;
with the proviso that the total number of carbons in the two acyl R$_2$ groups is at least 30;
X is a salt-forming anion;
R$_1$ is H, lower alkyl, hydroxyloweralkyl or benzyl; and
Y is an integer from 1 to 4.

20. A compound according to claim 1 wherein X is R$_3$SO$_4^-$, R$_1$CO$_2$, Z(CO$_2^-$)$_2$, (CO$_2^-$)$_2$, tartrate or CH$_2$(CO$_2^-$)$_2$.

* * * * *

UNITED STATES PATENT AND TRADEMARK OFFICE
CERTIFICATE OF CORRECTION

PATENT NO. : 5,128,473

DATED : July 7, 1992

INVENTOR(S) : Floyd E. Friedli, et al.

It is certified that error appears in the above-identified patent and that said Letters Patent is hereby corrected as shown below:

Column 11, line 64, Claim 8: "claim 2" should read as --claim 1--

Signed and Sealed this

Thirty-first Day of August, 1993

*Attest:*

BRUCE LEHMAN

*Attesting Officer*  *Commissioner of Patents and Trademarks*